(12) United States Patent
Wang et al.

(10) Patent No.: US 7,555,100 B2
(45) Date of Patent: Jun. 30, 2009

(54) LONG LENGTH IMAGING USING DIGITAL RADIOGRAPHY

(75) Inventors: Xiaohui Wang, Pittsford, NY (US); Richard Ruscio, Spencerport, NY (US)

(73) Assignee: Carestream Health, Inc., Rochester, NY (US)

( * ) Notice: Subject to any disclaimer, the term of this patent is extended or adjusted under 35 U.S.C. 154(b) by 117 days.

(21) Appl. No.: 11/613,289

(22) Filed: Dec. 20, 2006

(65) Prior Publication Data

US 2008/0152088 A1    Jun. 26, 2008

(51) Int. Cl.
G01N 23/04    (2006.01)
(52) U.S. Cl. .................................... 378/98.12
(58) Field of Classification Search ............... 378/98.12
See application file for complete search history.

(56) References Cited

U.S. PATENT DOCUMENTS

| | | | |
|---|---|---|---|
| 4,613,983 A | | 9/1986 | Yedid et al. |
| 5,123,056 A | | 6/1992 | Wilson |
| 5,337,341 A | * | 8/1994 | Shimizu ..................... 378/98.2 |
| 5,751,783 A | * | 5/1998 | Granfors et al. ............. 378/108 |
| 5,751,837 A | * | 5/1998 | Watanabe et al. ............ 378/165 |
| 6,055,295 A | * | 4/2000 | Murthy et al. .............. 378/151 |
| 6,215,853 B1 | * | 4/2001 | Kump et al. ................ 378/151 |
| 6,273,606 B1 | | 8/2001 | Dewaele et al. |
| 6,744,062 B2 | | 6/2004 | Brahm et al. |
| 6,895,076 B2 | | 5/2005 | Halsmer et al. |
| 6,895,106 B2 | | 5/2005 | Wang et al. |
| 6,944,265 B2 | | 9/2005 | Warp et al. |
| 2002/0147660 A1 | * | 10/2002 | Indence ....................... 705/26 |
| 2002/0159564 A1 | | 10/2002 | Wang et al. |
| 2002/0191750 A1 | | 12/2002 | Wang et al. |
| 2004/0101103 A1 | | 5/2004 | Warp et al. |
| 2004/0247081 A1 | * | 12/2004 | Halsmer et al. ............. 378/108 |
| 2005/0232397 A1 | | 10/2005 | Atzinger et al. |
| 2006/0193437 A1 | * | 8/2006 | Boeing et al. ............... 378/115 |

FOREIGN PATENT DOCUMENTS

EP    1 255 403 A2    11/2002
EP    1 484 016 A1    12/2004

* cited by examiner

Primary Examiner—Chih-Cheng G Kao

(57) ABSTRACT

A method for long length imaging with a digital radiography apparatus. Setup instructions are obtained for the image and a set of imaging positions is calculated for an exposure series according to the setup instructions. An operator command is obtained to initiate an imaging sequence. The imaging sequence is executed for each member of the set of imaging positions in the exposure series by automatically repeating the steps of positioning a radiation source and a detector at a location corresponding to the specified member of the set of imaging positions and obtaining an image from the detector at that location and storing the image as a partial image. The long length image is generated by combining two or more partial images.

20 Claims, 14 Drawing Sheets

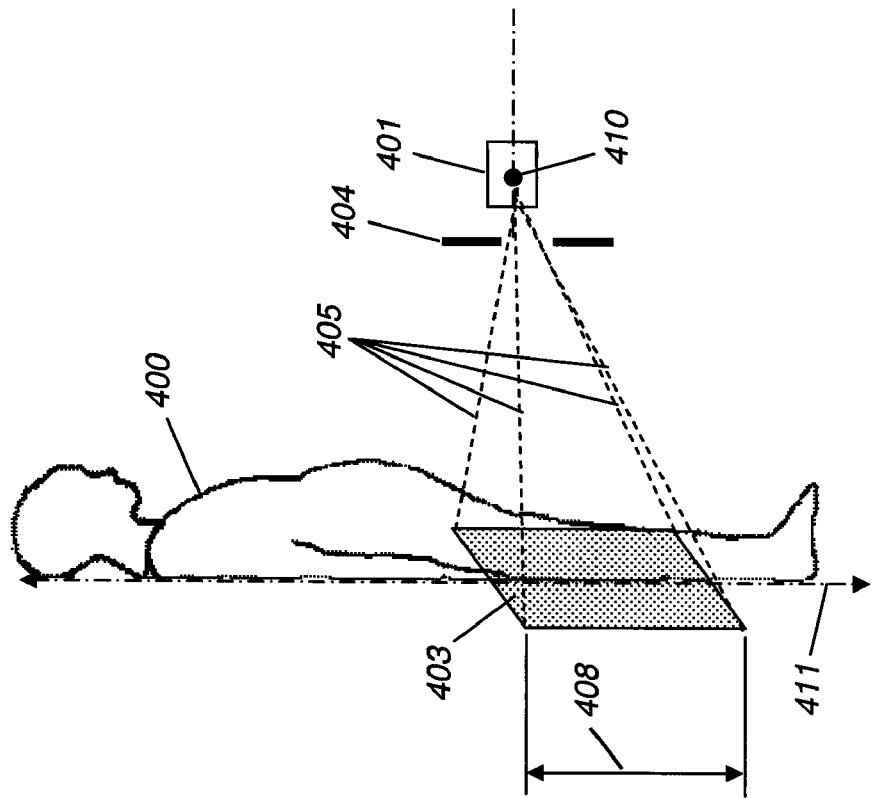
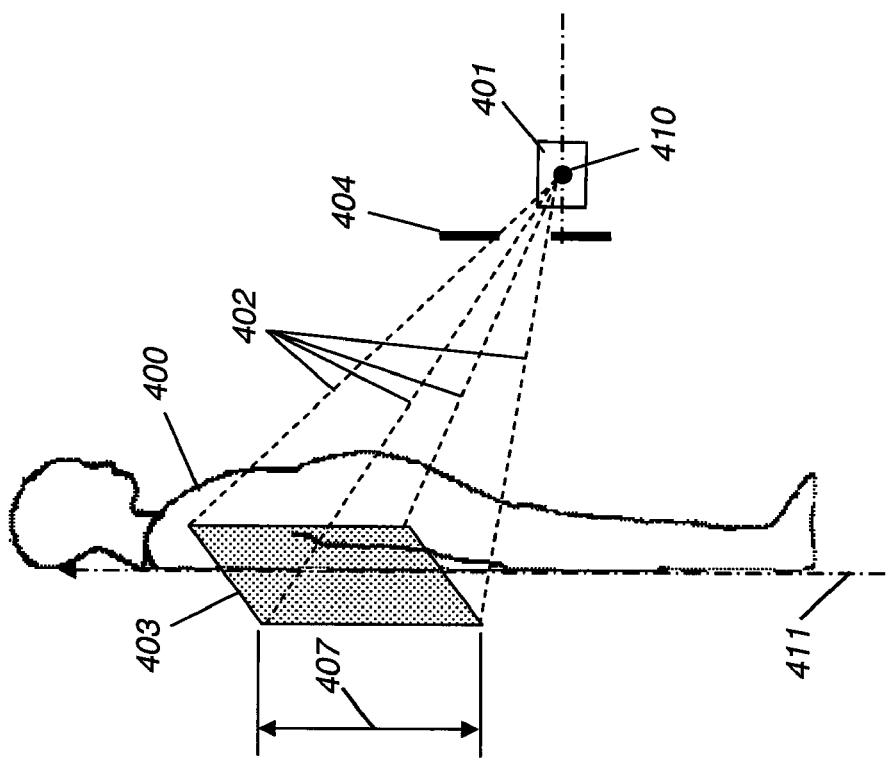

LONG LENGTH IMAGING USING DIGITAL RADIOGRAPHY

FIELD OF THE INVENTION

The invention generally relates to the integration of digital radiography projection x-ray hardware and software systems, and more particularly relates to a system and method for imaging a long length body part.

BACKGROUND OF THE INVENTION

Digital Radiography (DR) systems are being employed in medicine and industry, with particular value as clinical imaging tools. As shown in the simplified block diagram of FIG. 1 of a prior art system, radiation from a radiation source 12 in a DR imaging apparatus 10 is directed through a subject 14 and impinges on a radiation detector 30 that includes a scintillator screen 16 for converting the energy from ionized radiation into light radiation having a different frequency, typically within the visible spectrum, and an image sensing array 20. Image sensing array 20, typically mounted on the backplane of scintillator screen 16 or otherwise optically coupled with scintillator screen 16, forms a digital image from the emitted light that is excited by the incident radiation. The digital image thus formed can be processed and displayed by an image processing apparatus on a control logic processor 18, typically provided by a computer workstation and display 19.

Unlike conventional x-ray film apparatus, DR imaging apparatus 10 does not require a separate processing area, light-protected environment, or image processing consumables. An advantage of DR imaging technology is speed, since images are obtained substantially immediately after the x-ray exposure. As such, for medical applications, a diagnostic image can be provided to medical personnel while a patient is still present at an imaging facility.

In conventional x-ray film applications, there has been a continuing need for projection x-ray film media of sufficient size to image larger body parts. Body parts having a high length-to-width aspect ratio (e.g., the spine or a full leg) are film imaged using a technique called long length imaging (LLI). Observations and measurements from those films are useful for many conditions, such as in diagnosing scoliosis, where the Cobb Angle is measured, or measurements of leg length, angulation and deformity are obtained. To meet the demand for long length imaging, existing film screen cassette sizes up to 35 cm×130 cm can be used.

FIG. 2 shows a prior art conventional film imaging embodiment wherein both an x-ray tube 101 and a film cassette 103 are stationarily maintained during a long length imaging exam. The beam from x-ray tube 101 can be collimated to a desired x-ray coverage exposure area 102. An image of a patient 100 can then be acquired in a single exposure.

As FIG. 2 shows, film is advantaged for long length imaging since it can be provided in a large sheet when needed. In contrast, digital projection radiography, provided by both Computed Radiography (CR) and Digital Radiography (DR) systems, uses a fixed-size image detector. This makes long length imaging more difficult for both CR and DR systems. For example, flat panel DR plates are generally available in a small number of sizes, up to a maximum extent of about 43×43 cm. A detector of this size can image only a portion of the body part at a time and so is inadequate for performing imaging exams of longer length body parts such as the full spinal column or full leg.

Some CR apparatus address long length imaging. For example, Eastman Kodak Company provides stitching software and a cassette positioning system for LLI that delivers images up to 17 inches wide by 51 inches long (43×129 cm). This can be obtained using a single CR cassette or using multiple CR cassettes. However, CR cassettes require scanning apparatus in order to read the exposed image. So, while there is no longer a film processing step when using CR cassettes, there remains a scanning step and a process for erasure with CR cassette processing. The handling and identifying of the unprocessed cassette data that is not yet scanned creates workflow and data collection issues at some sites. Some CR long length imaging apparatus are described in U.S. Pat. No. 6,744,062 (Brahm), U.S. Pat. No. 6,895,106 (Wang), and U.S. Pat. No. 6,273,606 (Dewaele).

DR systems with flat-panel detectors offer some advantages over film-based and CR cassette systems with respect to workflow. However, the cost and technology constraints of DR panels limit detector size and complicate the task of long length imaging.

There have been some proposed long length imaging with DR systems. In general, these systems obtain a sequence of multiple exposures/images at varying positions, with the assumption that the patient remains still during the exam. The individual images are then stitched together to reconstruct a larger composite image.

FIG. 3 shows an exemplary technique, using tube and detector translation, for example as described in U.S. Pat. No. 5,123,056 entitled "WHOLE-LEG X-RAY IMAGE PROCESSING AND DISPLAY TECHNIQUES" to Wilson and U.S. Pat. No. 4,613,983 entitled "METHOD FOR PROCESSING X-RAY IMAGES" to Yedid et al. With this technique, the detector or the patient or both are translated along a path that allows collection of a sequence of partial images to be obtained. The final image of a longer length body part that exceeds the image acquisition area of the detector can be obtained from a composite of the individual partial images. As shown in FIG. 3, a patient 200 is exposed as defined by an x-ray tube first position 201 and a detector first position 203. A collimator of the x-ray tube is adjusted by the technologist such that an x-ray exposure area 202 can covers the detector while protecting the patient from unnecessary radiation in the non-imaging related regions. Subsequently, both the x-ray tube and the detector are translated in parallel along a tube axis of motion 210 and a detector axis of motion 211, respectively, to a second position, as indicated by an x-ray tube second position 206 and a detector second position 208. A second exposure of the patient is taken with the x-ray tube and detector in their second position, with x-ray exposure area 207 covering the detector. There may be an overlap between coverage areas for consecutive detector positions, in order to facilitate image stitching. This process for obtaining partial images is continued until the full length of the body part to be examined has been imaged.

While the sequence described with reference to FIG. 3 can allow a larger image to be formed from separate smaller images, there are some disadvantages. For example, an apparatus providing movement of both the detector and the x-ray tube can be mechanically complex. Some amount of geometric distortion is inherent with such an arrangement, which can make it difficult to obtain precise image stitching. The severity of the image-stitching problem can increase with increasing thickness of the body part.

FIGS. 4A and 4B show another method for field translation based on x-ray tube angular rotation, such as that described in commonly assigned U.S. Patent Application Publication No. 2002/0159564 entitled "METHOD FOR ACQUIRING A RADIATION IMAGE OF A LONG BODY PART USING DIRECT DIGITAL X-RAY DETECTORS" by Wang et al.

Using a detector 303 positioned at first position 307, a patient 300 is exposed to x-rays 302 from and x-ray tube 301 having an axis of rotation about a point 3 10. X-ray tube 301 is directed toward detector 303. Detector 303 is translated along a detector axis of motion 311 between each exposure, while x-ray tube 301 is rotated about point 310 between each exposure. For example, with detector 303 positioned at second position 308, the x-ray tube (shown in FIG. 4B as x-ray tube 304) is rotated about point 310, and patient 300 is exposed to x-rays 305. Following image acquisition, the individual images are stitched together as if the whole image had been acquired with a single x-ray exposure using the film geometry of FIG. 2.

FIGS. 5A and 5B show another method for field translation using a collimation shutter 404 mounted adjacent an x-ray tube 401, as described in commonly assigned U.S. Patent Application No. 2002/0191750 entitled "COLLIMATION DEVICE AND METHOD FOR ACQUIRING A RADIATION IMAGE OF A LONG BODY PART USING DIRECT DIGITAL X-RAY DETECTORS," by Wang et al. A focal point 410 is provided for exposing a patient 400 and capturing the image using detector 403. The x-ray tube remains stationary, and collimator shutter 404 translates to an appropriate position to redirect the emitted x-rays. Detector 403 translates along an axis 411 to receive the x-rays. Collimation shutter 404 has a particular size opening, and moves adjacent x-ray tube 401 to selectively expose the portion of the patient adjacent the detector. For example, at a first position 407 receiving a first x-ray exposure 402, and then at a second position 408, receiving a second x-ray exposure 405.

The individual images can be "stitched together" (i.e., combined) to form a full size image of a long length body part. For example, U.S. Pat. No. 6,944,265 entitled "IMAGE PASTING USING GEOMETRY MEASUREMENT AND A FLAT-PANEL DETECTOR" to Warp et al. describes a process for forming a composite image from individual image segments. U.S. Pat. No. 6,895,076 entitled "METHODS AND APPARATUS FOR MULTIPLE IMAGE ACQUISITION ON A DIGITAL DETECTOR" to Halsmer et al. describes a system for long length imaging that includes operator identification of top and bottom (start and stop) positions, calculations for overlap between successive images, an imaging operation controller that controls x-ray source operation, and a position changing apparatus for changing the relative position of the x-ray source and the subject of interest.

Matching the capabilities of conventional film-based systems for long length imaging continues to pose a challenge to DR system design and operation. For example, obtaining a long length image with conventional DR systems remains operator intensive. The operator monitors and controls each movement or set of movements that adjust the position of the x-ray source and detector mechanisms. Exposure settings for each individual image require operator attention. Even though images may be stitched together with some degree of automation, there remain considerable demands on operator time and attention for long length DR imaging. There exists a need for a system providing seamless integration of operator control, user interface, software function, and hardware movement. Such a system would mimic the operator workflow used in screen-film systems.

SUMMARY OF THE INVENTION

It is an object of the present invention to provide a method for long length imaging with a digital radiography apparatus comprising: obtaining setup instructions for the image; calculating a set of imaging positions for an exposure series according to the setup instructions; obtaining an operator command to initiate the exposure series; executing an imaging sequence for each member of the set of imaging positions in the exposure series by automatically repeating the steps of: (i) positioning a radiation source and a detector at a location corresponding to the specified member of the set of imaging positions; (ii) obtaining an image from the detector at said location and storing the image as a partial image; and generating the long length image by combining two or more partial images.

The present invention can provide an automated method for long length imaging that is suited to DR imaging apparatus.

The present invention can reduce the need for oversize film. The method of the present invention simplifies the long length imaging process for users of DR imaging apparatus.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

FIGS. 5A and 5B are block diagrams showing prior art use of a shutter mechanism for adjusting an exposure area.

DETAILED DESCRIPTION OF THE INVENTION

The present invention provides a method and apparatus that automate long length imaging using a DR imaging apparatus and minimize operator interaction during the imaging sequence. The present invention provides for a long length imaging sequence to be executed once set up and initiated by the operator, and provides automatic adjustment of exposure controls during the long length imaging session. It is to be understood that elements not specifically shown or described herein may take various forms well known to those skilled in the art.

Figure 14:
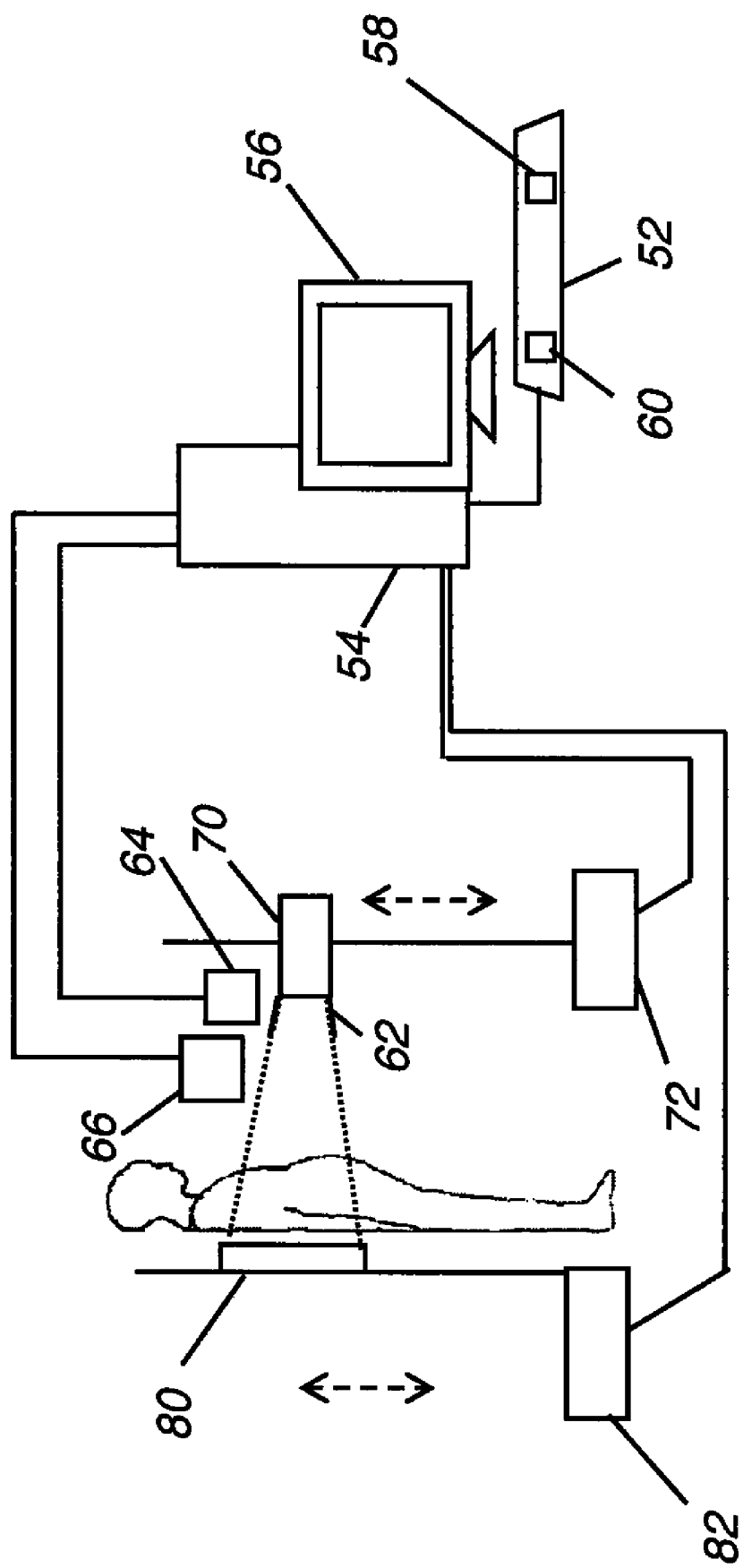
FIG. 14 is a block diagram showing an apparatus for automated imaging according to one embodiment of the present invention.

FIG. 14 shows an imaging apparatus 50 suitable for practicing the method of the present invention. A collimator 62 is provided which can change it opening size by an actuator 66 that is in communication with a control logic processor 54. A sensor 64 indicates the position of collimator 62 to control logic processor 54. Processor 54 can be in communication with a display 56. Other sensing apparatus (not shown in FIG. 14) provide information on the distance between x-ray emitter 70 and detector 80. A transport apparatus 72, or other device more generally termed a field translation apparatus, controls the position of x-ray emitter 70, while a transport apparatus 82 controls the position of detector 80. A start button 58 and cancel button is provided on the system control panel 52.

Figure 6:
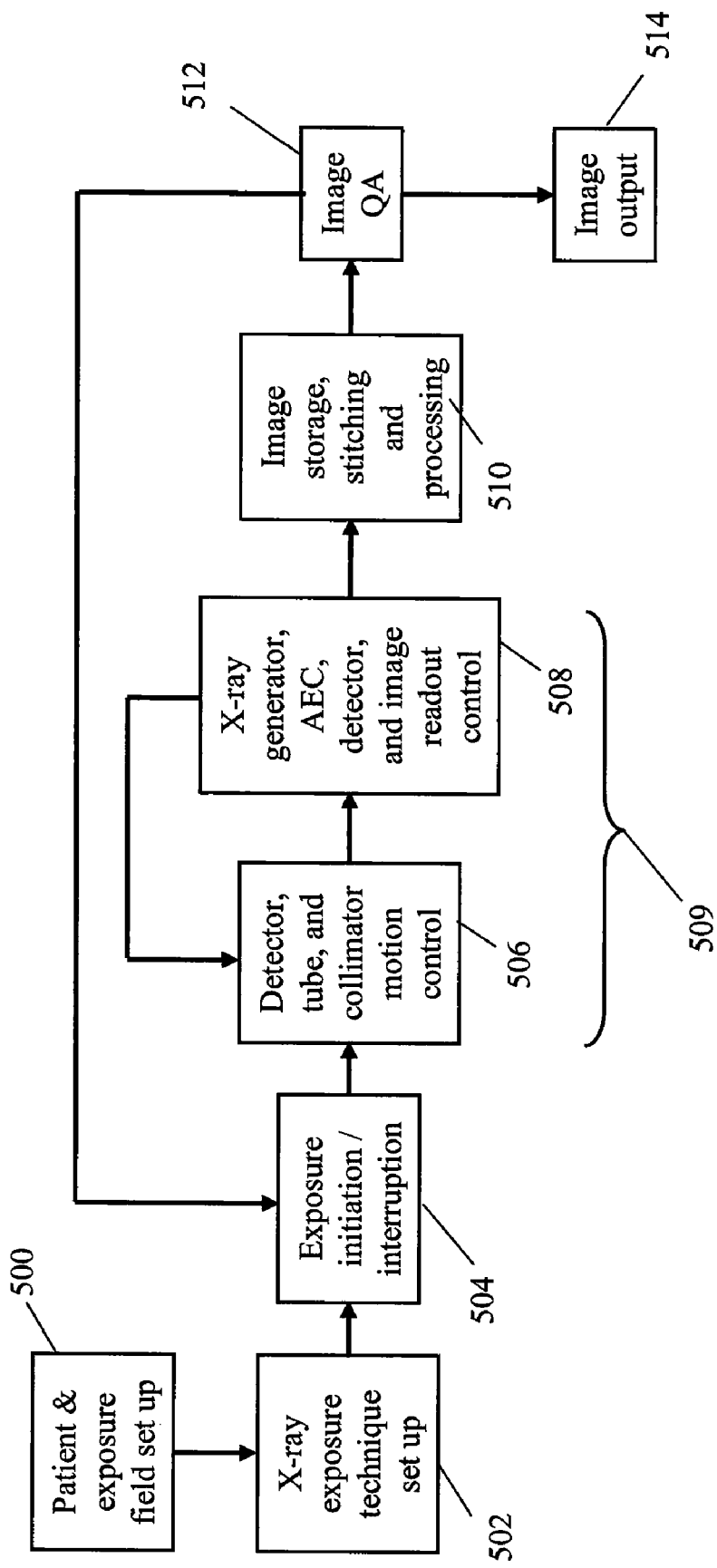
FIG. 6 is a logic flow diagram for automated imaging operation according to one embodiment of the present invention.

The logic flow diagram of FIG. 6 shows the general steps for long length imaging using the method of the present invention.

Figure 1:
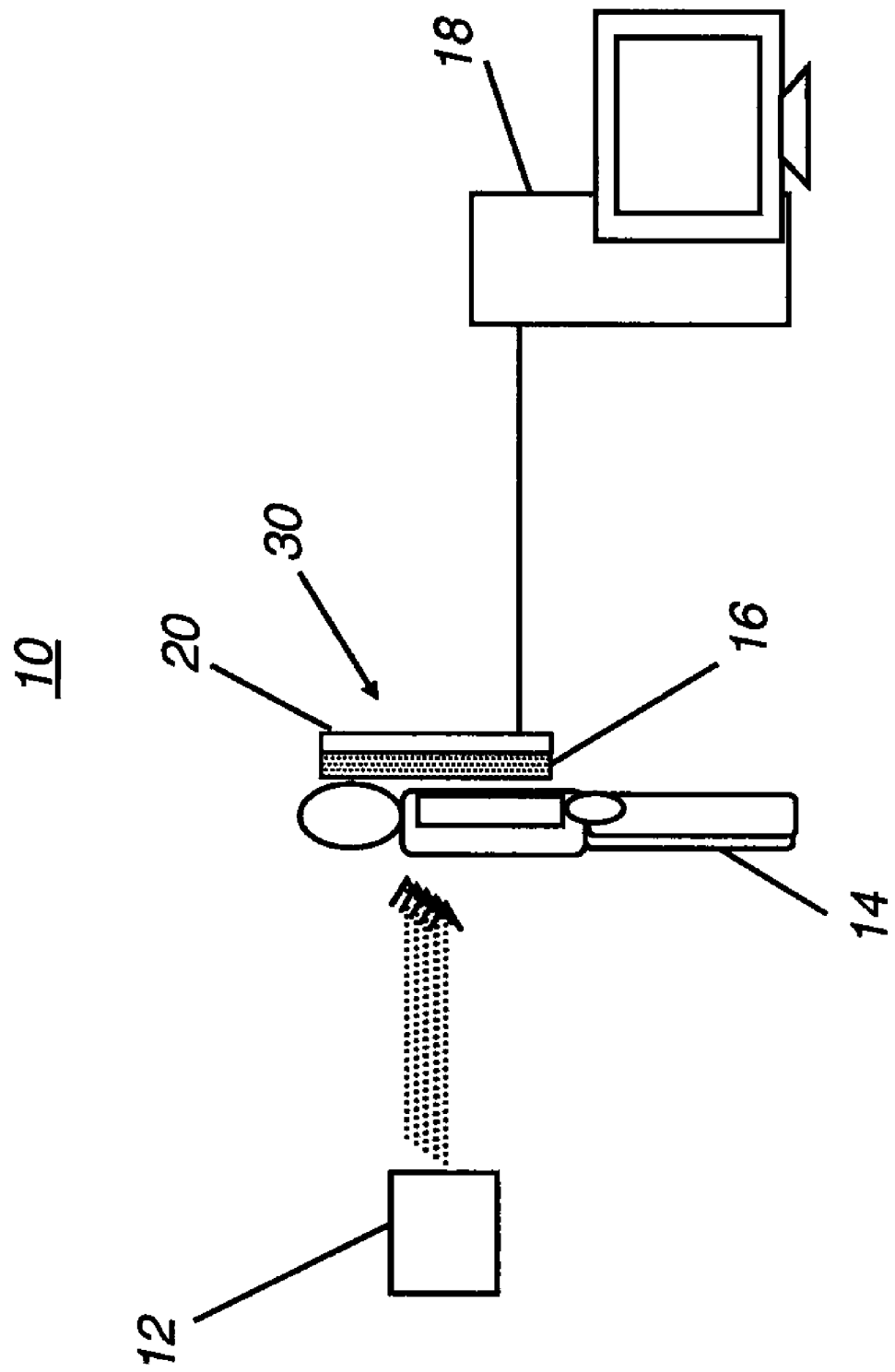
FIG. 1 is a block diagram showing key components of a prior art digital radiography imaging apparatus.
Figure 2:
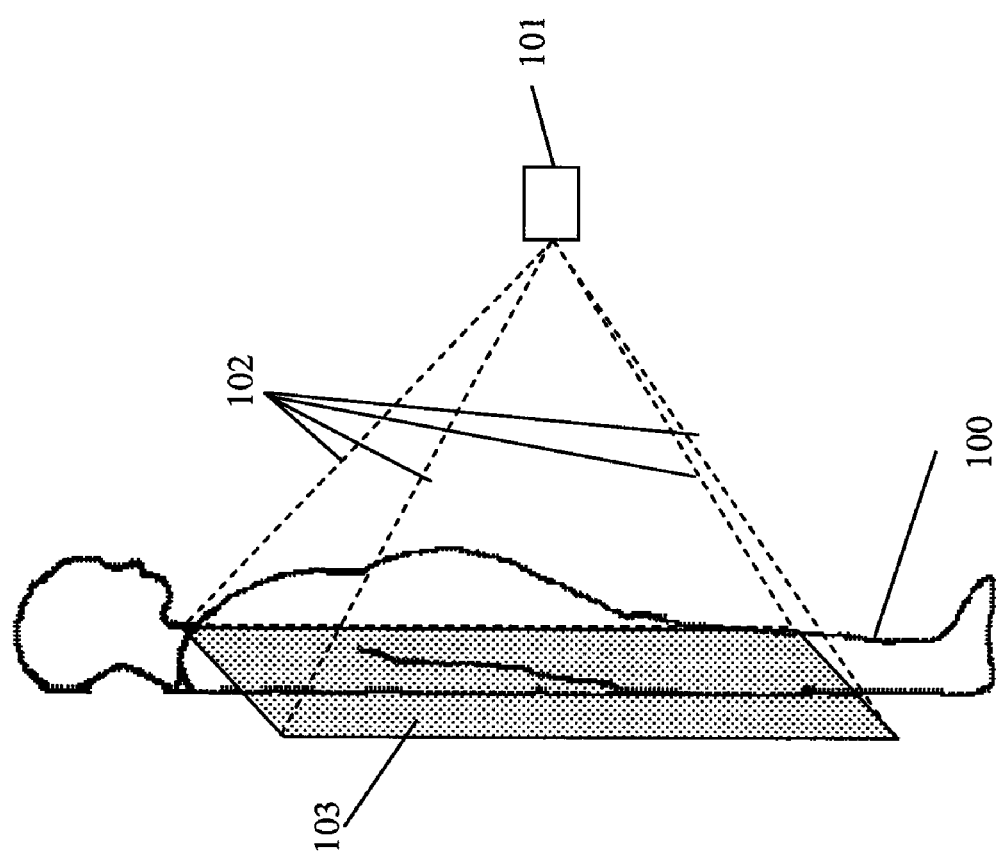
FIG. 2 is a block diagram showing long length imaging using a conventional film-based radiography system.
Figure 3:
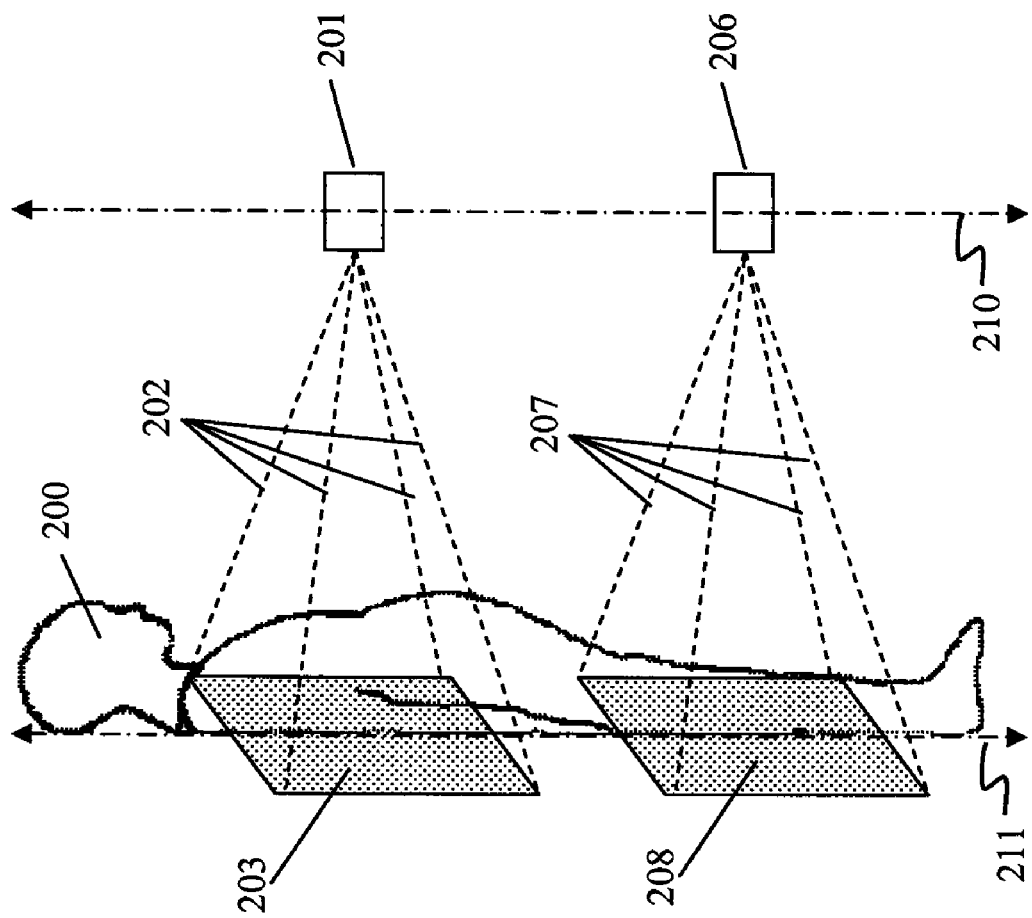
FIG. 3 is a block diagram showing long length imaging using a prior art DR imaging apparatus.

In a setup step 500, the radiation technologist (e.g., user) positions the patient (for example, in an upright or supine orientation) appropriate to the exam requirements. Using system controls of the embodiment of the present invention, the technologist identifies a desired exposure technique setup. For example, the user sets an initial x-ray tube height, and uses the visible light of the collimator aperture to cover the full desired anatomical regions of the patient. The visible light from the x-ray collimator, which is representative of the full, actual x-ray exposure coverage, assists the technologist in determining the total exposure area on the patient. This process is the similar to that used for the screen film system of FIG. 2. The system of the present invention uses the area marked by visible light as the system controlled exposure area as well. Note that, in setup step 500, the collimator size exceeds the dimensions of the full sized exposure field. Positional and component distance feedback, including information about collimator size, is provided to control logic for the imaging system. This allows computation of the number of exposures needed in an exposure series and the actual exposure size, as is described subsequently. Thus, a special (long length imaging) mode of system operation is used for setup step 500. In this special mode, the collimator opening is deliberately allowed to exceed the detector size in order to provide the needed measurement for long length imaging.

In an x-ray exposure technique setup step 502, the technologist determines and sets up the overall x-ray technique parameters that provide instructions for imaging, including but not limited to kVp, mAs, automatic exposure control (AEC) usage, exposure compensation factor (ECF), beam filtration, and anti-scatter grid settings. In film screen radiography for full-spine and full-leg exams, a specially built beam intensity compensation filter is commonly used to pre-attenuate the beam intensity such that the exposure on the film is more uniform across the whole patient anatomy for optimal film brightness and contrast, and to reduce unnecessary x-ray radiation to thinner parts of the patient anatomy. With the system of the present invention, since only a portion of the patient anatomy is imaged at any one time, the compensation filter usage is typically not employed. Rather, the system of the present invention can use the AEC to automatically adjust the x-ray output during long length imaging. In a preferred embodiment of the present invention, the AEC is used when acquiring each image of the exposure series.

In an exposure initiation/interruption step 504, the technologist initiates the full exposure series by a single command entry, for example, by pressing an exposure button on a system control console. The system of the present invention automatically performs the steps required for the exposure series, including, but not limited to, positioning the detector, the X-ray tube, and the collimator for imaging at the first location for the series, adjusting the collimator aperture, preparing the x-ray detector to the ready state, starting the x-ray exposure, and reading out the image from the detector. The system can repeat the process for the subsequent imaging positions in order to acquire all the images. When the setup instructions have been received, the system determines the motion control at motion control step 506. Continuous execution of motion control step 506 and an x-ray generator, AEC, detector, and image readout control step 508 is performed. As shown in FIG. 6, a loop 509 can be executed, with as many repetitions of steps 506 and 508 as are necessary in order to obtain the set of n images for stitching in an image storage, stitching, and processing step 5 10. Each of the n members of the set of partial images that is obtained can then be stitched into the final long length image.

An optional image quality assurance (QA) step 512 and an image output step 514 are also executed as part of long length image processing according to one embodiment.

The system of the present invention preferably provides two modes of operation: a fully automatic operation (e.g., for which one button press or other command entry initiates the full sequence to obtain all exposures in the exposure series in an automated mode) and a semi-automatic operation (e.g., in which each exposure in the series requires a separate affirmation from the operator by button press or other command entry). If, for a particular reason, the technologist determines that the exposure sequence should be stopped earlier (for example, for a patient condition or safety concerns), the operator can press the exposure button again or enter an appropriate command to interrupt and stop the process in the fully automatic operation mode.

To facilitate image stitching, in a preferred embodiment of the present invention, encoders or other suitable types of sensors are used to control and detect position and operation of various mechanical components of the system and their operating parameters, including, but not limited to, the detector position, tube position, tube rotation angle, collimator aperture size, and collimator shutter position.

Determination of Mechanical Movement

Referring again to FIG. 6, when the setup instructions have been received, the system determines the motion control at motion control step 506. For example, the system automatically calculates a set of imaging positions for an imaging exposure series, determines the number of exposures needed for an exposure series, determines the detector/tube/collimator stop positions for each image in the series, determines the effective exposure field size on the detector, and determines the collimator aperture size for each imaging position.

Figure 7:
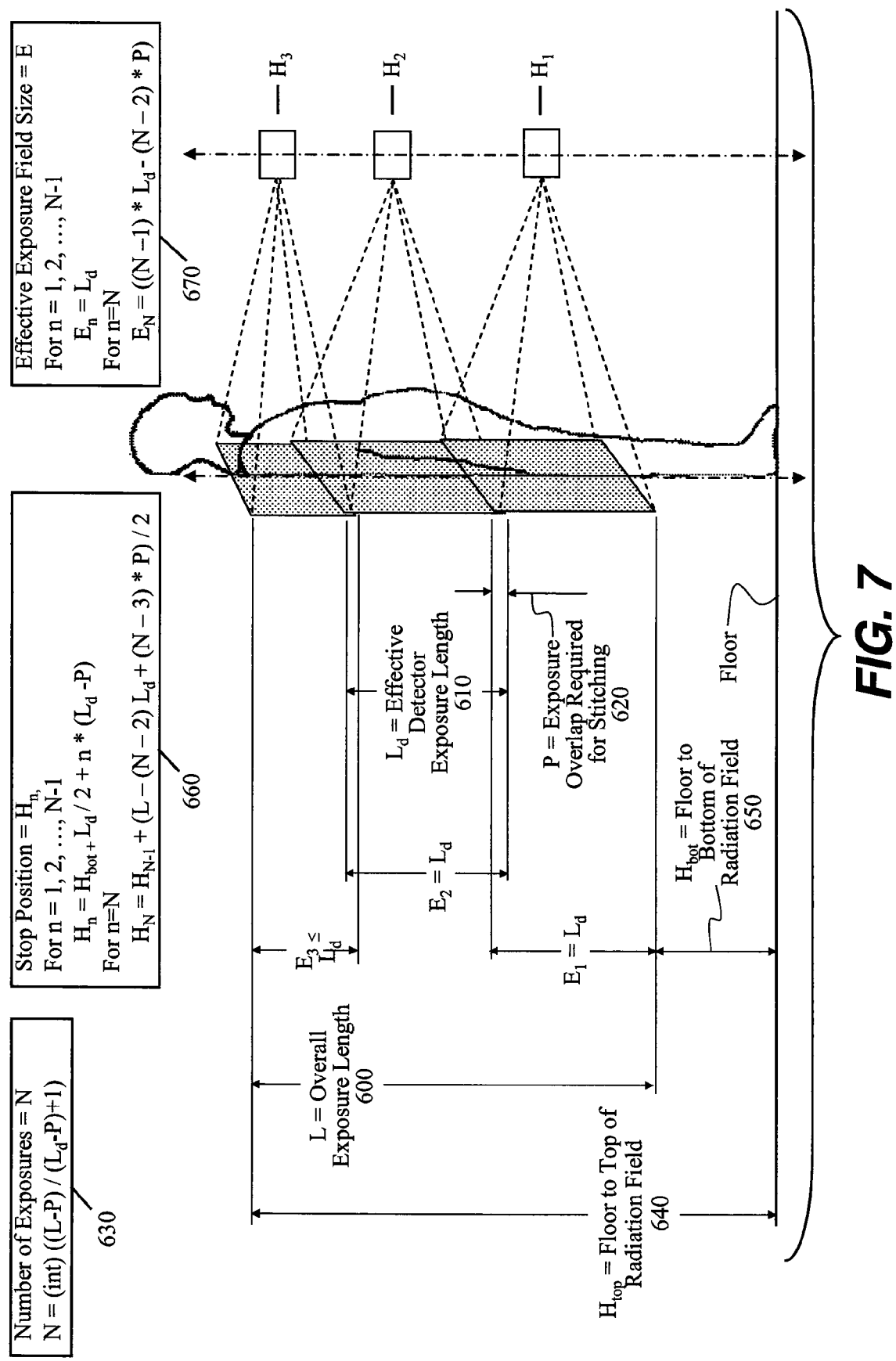
FIG. 7 is a schematic diagram showing dimensions and calculations performed for translation of the detector and x-ray source over a large field.

The method is described and expanded in detail in the schematic diagram of FIG. 7.

In the embodiment of FIG. 7, the imaging detector, x-ray tube, and collimator hardware form a field translation apparatus. The system appropriately positions the imaging detector, the x-ray tube (that acts as the radiation source), and the collimator hardware. The system includes feedback mechanisms that allow the system to detect and record the physical positions of the various devices. For example, optical encoders can be used as one type of feedback sensor.

If an overall exposure length 600 is L (as determined in step 500 of FIG. 6), an effective exposure length 610 on the detector per exposure is $L_d$, and the minimum exposure overlap 620 that is required for stitching is P. In the example shown in FIG. 7, the number of exposures 630 can be computed as follows:

$$N=(\text{int})((L-P)/(L_d-P)+1)$$

wherein the (int) operator takes the integer part of the result.

In step 500 (shown in FIG. 6), the x-ray technologist initially establishes the height of the image area by specifying at least two variables:

(i) A floor to top of radiation field 640 $H_{top}$
(ii) A floor to bottom of radiation field 650 $H_{bot}$ This is accomplished by adjusting the collimator so that the visible collimator light illuminates the full field desired for imaging. Sensors on the collimator itself can report the size of the collimator opening to system logic. This data can then be used in combination with other information on source-to-detector distance in order to determine the full extent of the image area.

A stop position 660 of the center of the detector and the x-ray tube is determined by:

$$H_n=H_{bot}+L_d/2+n\times(L_d-P), \text{ when } n=1, 2, \ldots, N-1,$$

wherein n refers to the nth image of the exposure sequence.

For the last exposure, N, the position is calculated separately. It is noted that the last exposure of the exposure series will have an exposure field smaller than $L_d$, to not unnecessarily expose the patient anatomy outside the specified area.

For the last exposure, the stop position of the center of the detector and the x-ray tube is given by:

$$H_N=H_{N-1}+(L-(N-2)L_d+(N-3)P)/2.$$

The effective exposure field size 670 on the detector is the same, $L_d$, for the first N−1 exposures, but can become smaller for the last exposure:

$$E_n=L_d \text{ when } n=1, 2, \ldots N-1$$

and $$E_N=-((N-1)L_d-(N-2)P).$$

Figure 8:
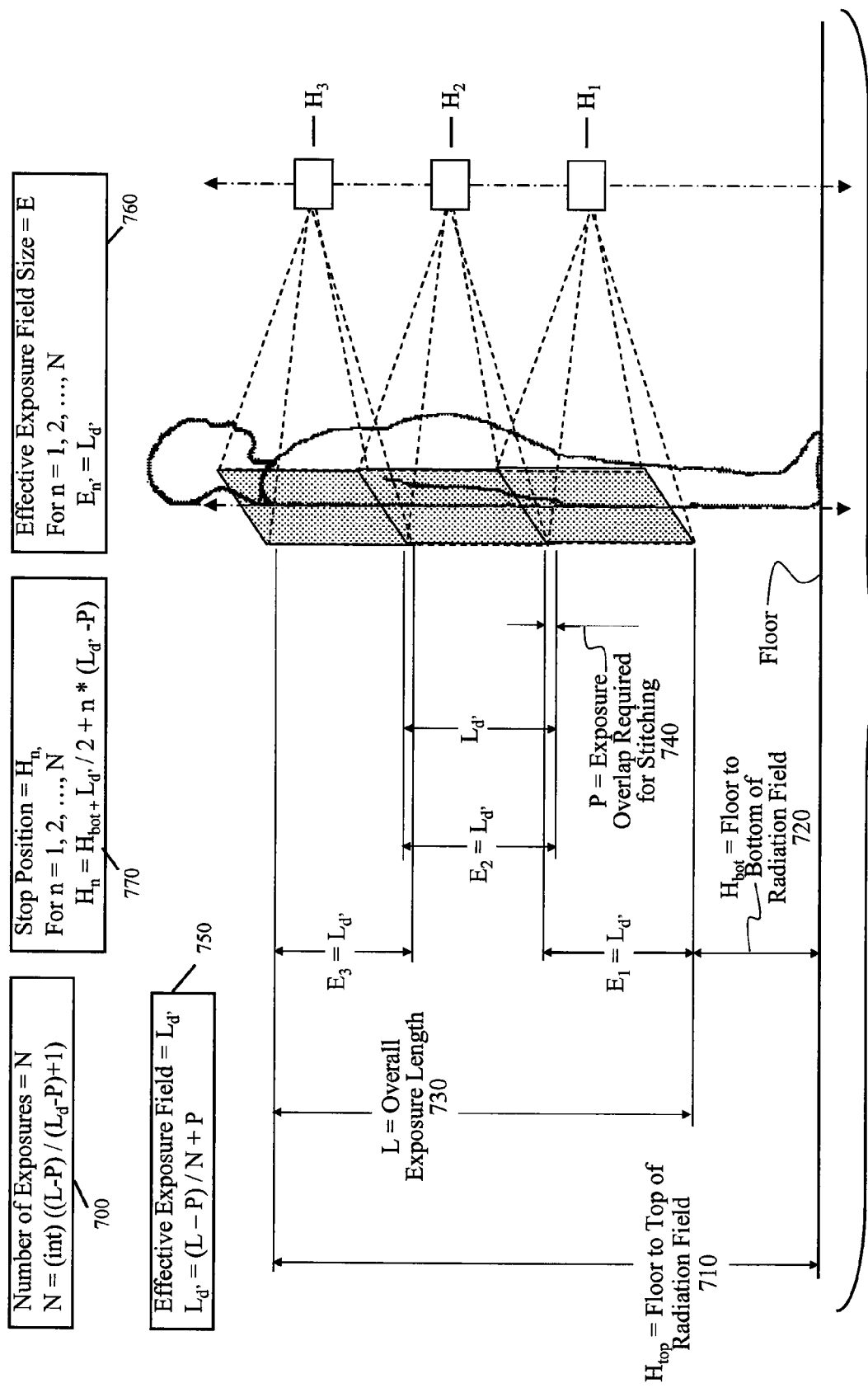
FIG. 8 is a schematic diagram showing an alternate set of dimensions and calculations performed for translation of the detector and x-ray source over a large field.

It can difficult for the system to adjust the detector/tube stop position (given non-equal travel distance), as well as the x-ray collimation field size (given non-equal field size), accordingly for each exposure. The schematic diagram of FIG. 8 shows a system embodiment of the present invention which provides for exposures with equal collimation field size, and equal detector and tube travel distance, during the exposure series.

The following are computed as was described with reference to the example of FIG. 7: a number of exposures 700 required, a top 710 and a bottom 720 of the radiation field, an overall exposure length 730, and a minimum exposure overlap required for stitching 740. The exposure fields are of equal size, and are obtained by setting an effective exposure field size 750 to:

$$L_d=(L-P)/N+P.$$

In this method, an effective radiation field 760 $E_{n'}$ (n=1, 2 ... N) will be the same, for all the exposures.

$$E_{n'}=L_d.$$

The calculation of tube/detector stop positions $H_n$ 770 (for n=1, 2, ... N) is accomplished by:

$$H_n=H_{bot}+L_d/2+n\times(L_d-P)$$

Figure 9:
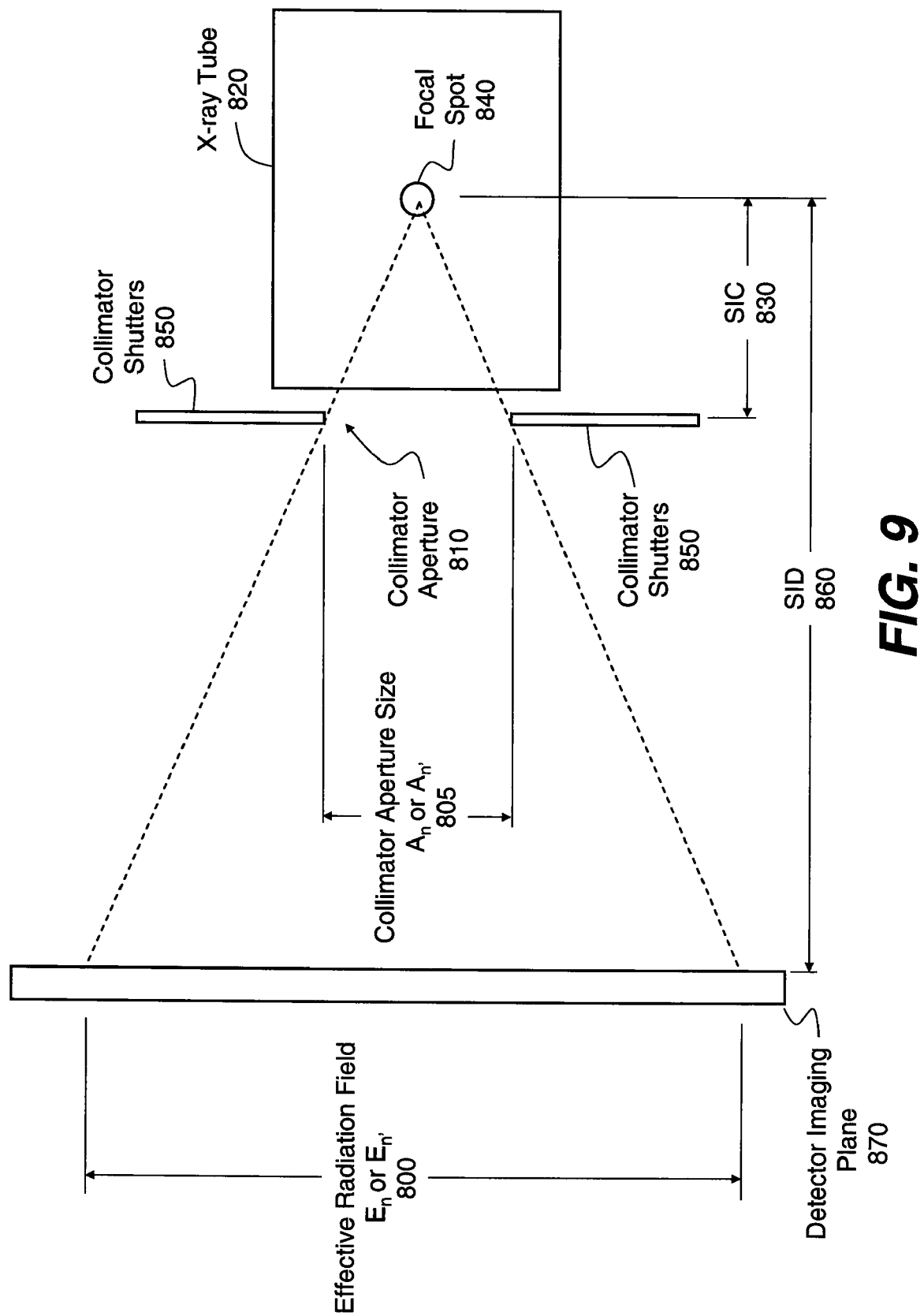
FIG. 9 is a schematic diagram showing key dimensions for obtaining an image at the detector.

FIG. 9 illustrates how the appropriate aperture size can be determined.

The size of an effective radiation field 800, $E_n$ or $E_{n'}$, is manipulated by modifying a collimator aperture 810 disposed adjacent x-ray tube 820. Assuming the collimator has a symmetric aperture around the central x-ray beam (which is common in conventional collimator design), an appropriate collimator aperture size 805 can be calculated based on the effective exposure field and the magnification factor:

$$A_n=E_n\times SIC/SID$$

or $$A_{n'}=E_{n'}\times SIC/SID$$

wherein SIC 830 is the distance between an x-ray focal spot 840 to collimator shutters 850, and SID 860 is the distance between x-ray focal spot 840 to a detector imaging plane 870.

Figure 10:
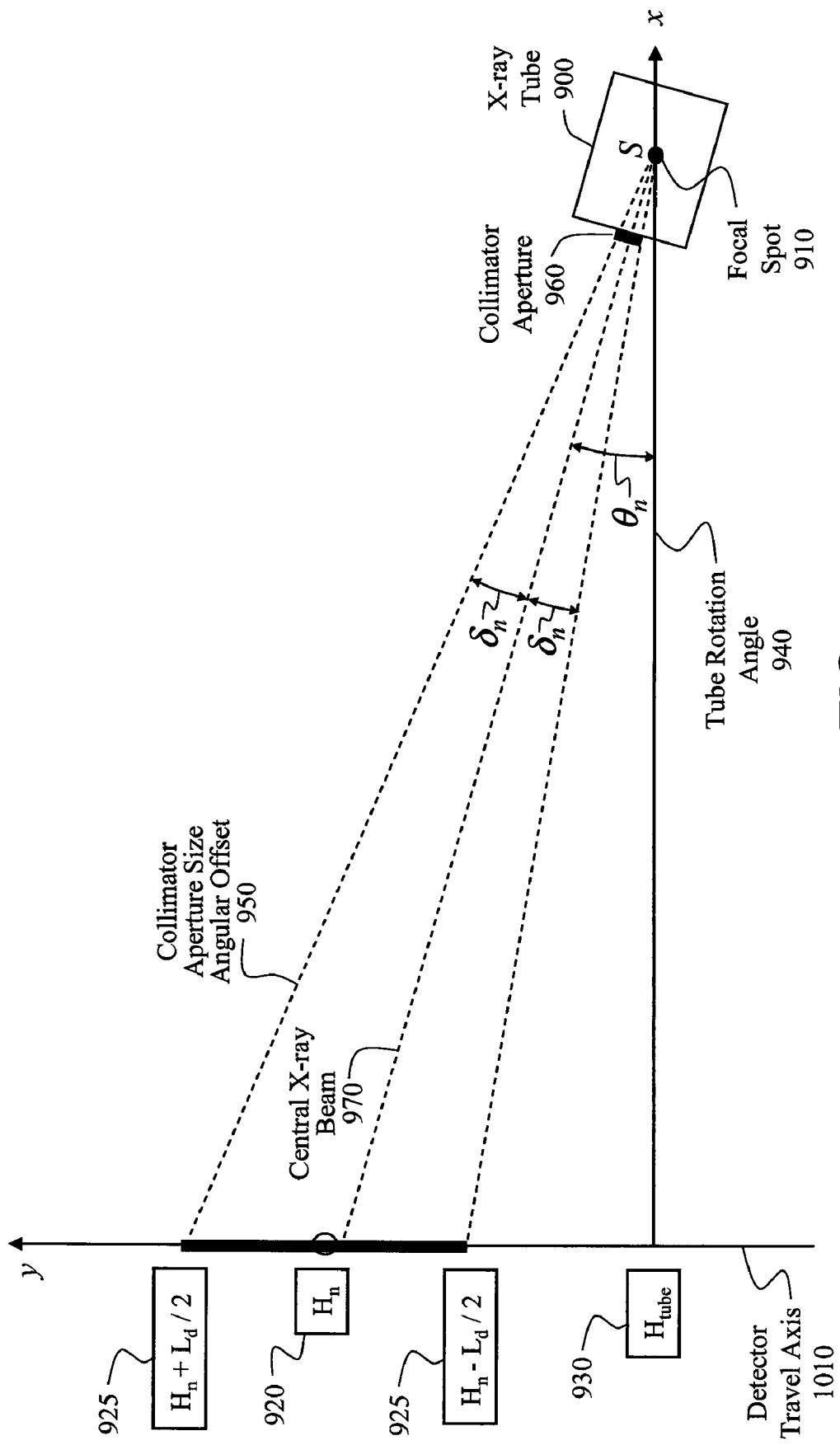
FIG. 10 is a schematic diagram showing angular relationships for x-ray imaging in one embodiment.

For the angular adjustment method for field translation described with reference to FIGS. 4A and 4B, the tube rotation angle and collimator aperture size would need to be specified. FIG. 10 shows the variables for the specification. The calculations of the number of stop positions, N, the detector stop positions, a detector stop position 920 $H_n$, the effective exposure length on the detector $L_d$, top and bottom of the radiation field, $H_{top}$ and $H_{bot}$ distance from the floor of the exam room, are as described above. An x-ray tube 900 is positioned such that its focal spot 910 is located at a height 930 labeled $H_{tube}$, the distance from the room floor:

$$H_{tube}=(H_{top}+H_{bot})/2$$

A collimator having symmetric aperture yields the following functions, for n=1, 2, ... N, from which can be calculated the values of $\theta_n$ for a tube rotation angle 940, and $\delta_n$ for the collimator aperture size angular offset 950 from a central x-ray beam 970:

$$(\tan(\theta_n+\delta_n)+\tan(\theta_n-\delta_n))\times SID/2=H_n-H_{tube}$$

and $$(\tan(\theta_n+\delta_n)-\tan(\theta_n-\delta_n))\times SID=E_n \text{ (or } E_{n'})$$

Exposure field top and bottom 925 is computed as shown in FIG. 10. In particular, a collimator aperture 960 size is:

$$A_n=2\times SIC\times\tan(\delta_n).$$

The aperture size would be reduced as the tube rotation angle increases to compensate for the gradually increasing magnification of the radiation field size.

Figure 4B:
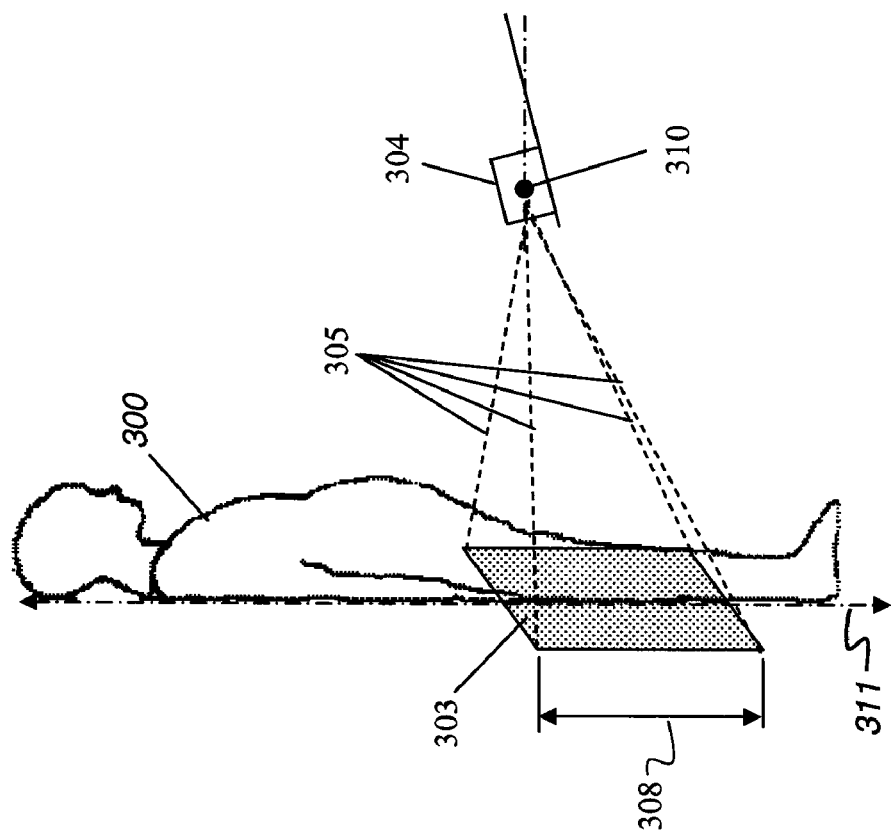
FIGS. 4A and 4B are block diagrams showing different imaging operations used for long length imaging with prior art DR apparatus.
Figure 4A:
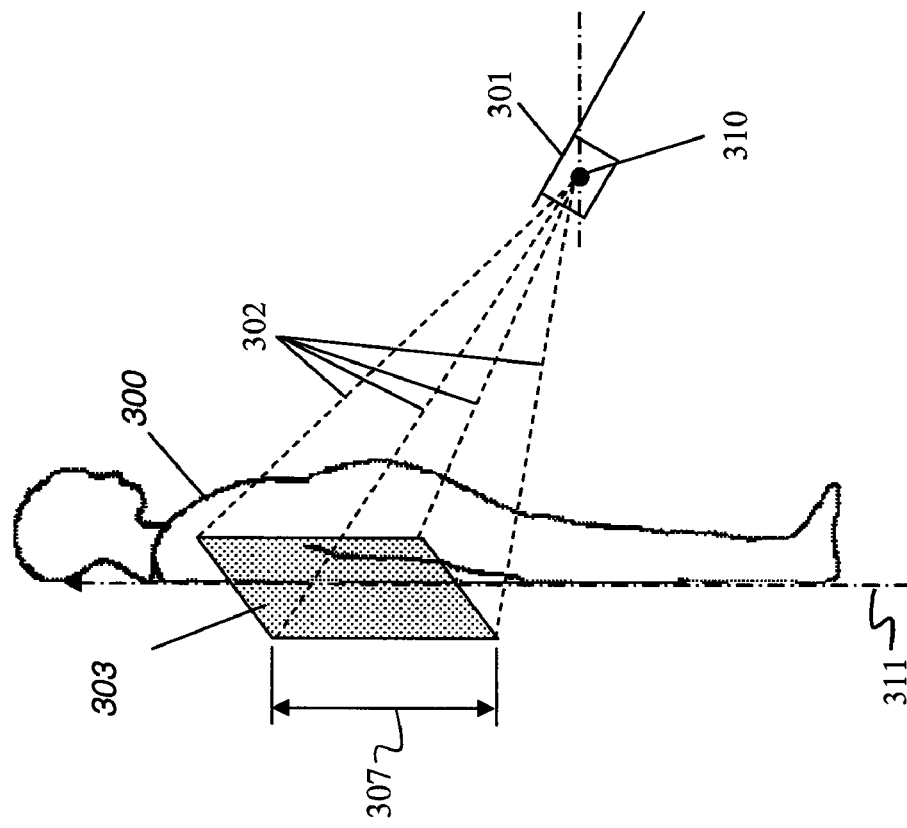
Figure 11:
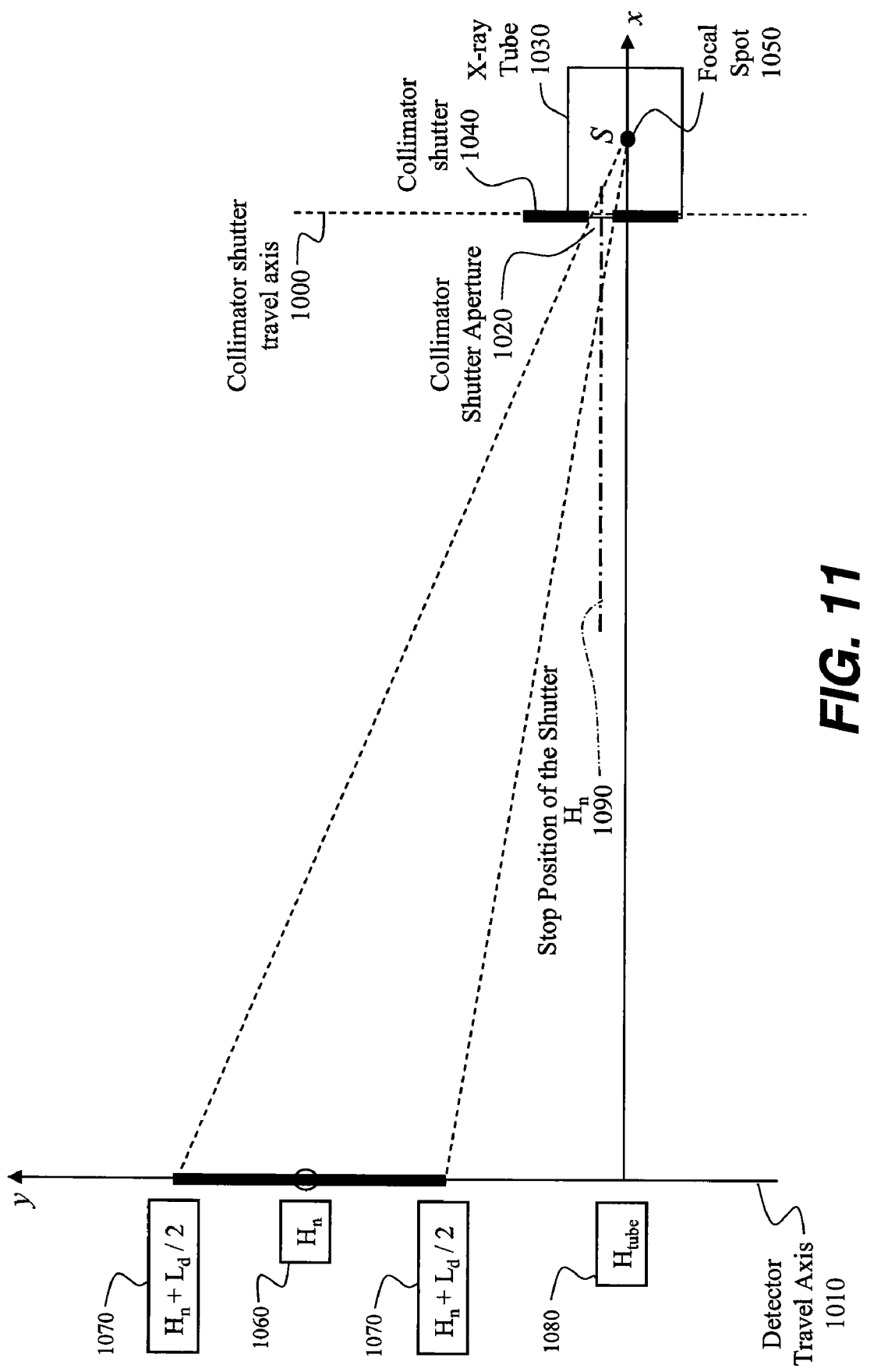
FIG. 11 is a schematic diagram showing use of the collimator shutter to define the image area.

The method shown in FIGS. 5A and 5B is similar to the method of FIGS. 4A and 4B in that the detector stop positions and the tube focal point locations are the same. As is shown in FIG. 11, an x-ray tube 1030 does not move, rather, a collimator shutter 1040 moves in front of the tube to selectively allow x-rays to exposure the detector at different locations. Therefore, the collimator shutter position and aperture size are specified. FIG. 11 shows the relevant information. Assuming a collimator shutter travel axis 1000 is parallel to a detector travel axis 1010, a collimator shutter aperture 1020 size is given by:

$$A_n=E_n\times SIC/SID \text{ or } A_{n'}=E_{n'}\times SIC/SID.$$

The stop position of the shutter relative to the tube focal spot is:

$$h_n = (H_n - H_{tube}) \times SIC/SID.$$

As noted earlier, FIG. 14 shows imaging apparatus 50, which can be configured for semi-automated and/or fully automatic operation. A technician enters the necessary imaging setup data during X-ray exposure technique set up step 502 (FIG. 6). The operator then begins exposure initiation/interruption step 504 by entering a start command at control panel 52, for example, using start button 58. When initiated, control of the imaging process passes to control logic processor 54, such as a dedicated processor or specially configured workstation. The operator can stop the process by activating cancel button 60; otherwise, continuous execution of motion control step 506 and an x-ray generator, AEC, detector, and image readout control step 508 (FIG. 6) is performed, as controlled by control logic processor 54. Steps 506 and 508 can repeat as is necessary to obtain the needed component images that are stitched together to form the final, full-length image.

For each imaging step, transport apparatus 72, or other device more generally termed a field translation apparatus, is controlled to position x-ray emitter 70 appropriately for that portion of the image. In the embodiment of FIG. 14, transport apparatus 82 is also controlled so that it positions a detector 80 at a suitable position for obtaining the image. Thus, as shown in FIG. 6, loop 509 can be executed, with as many repetitions of steps 506 and 508 as necessary to obtain the set of n images for stitching in an image storage, stitching, and processing step 510. Each of the n members of the set of partial images that is obtained can then be stitched into the final long length image.

Another embodiment allows the operator to step through the long length imaging sequence with multiple presses of start button 58 or other command entry mechanism. An alternative command entry mechanism includes, for example, an audio command, a button press, a touchscreen command, or a mechanical switch actuation. With one alternate method, a prompt is provided to the operator after initial setup is complete and following each of the steps to obtain a single partial image. Before or after movement of the imaging apparatus to the next position, the operator provides confirmation to continue by pressing start button 58; this initiates movement to the next position and capture of the next partial image therefrom. With this alternate method, the operator can exercise slightly greater control over the imaging sequence.

Image Stitching

Figure 12:
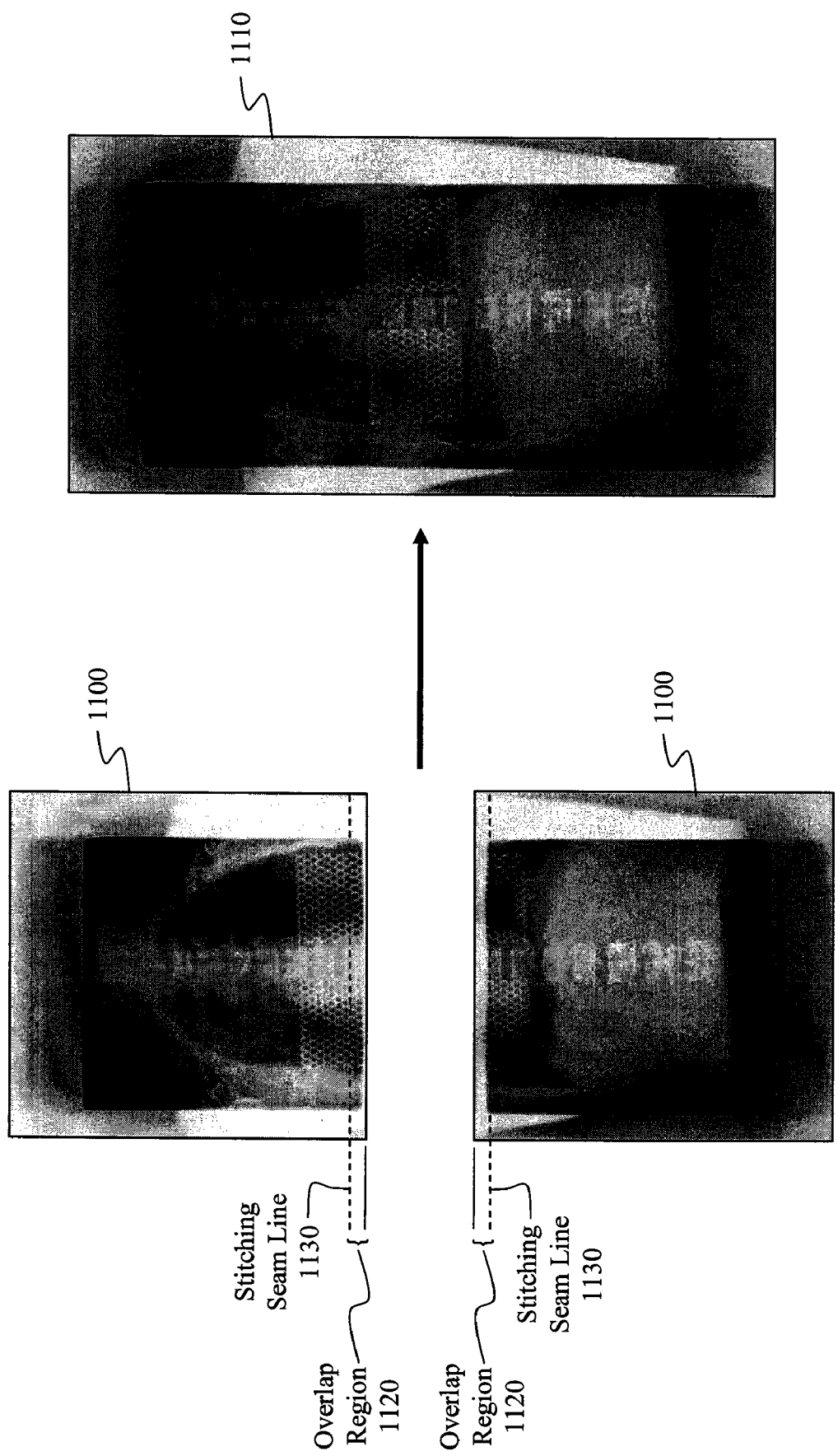
FIG. 12 is a view showing key parameters for image stitching.

FIG. 12 shows an example of two individual sub-images 1100 and the stitched final composite image 1110. Overlap regions 1120 are shown in sub-images 1100, as is stitching seam lines 1130.

Figure 13:
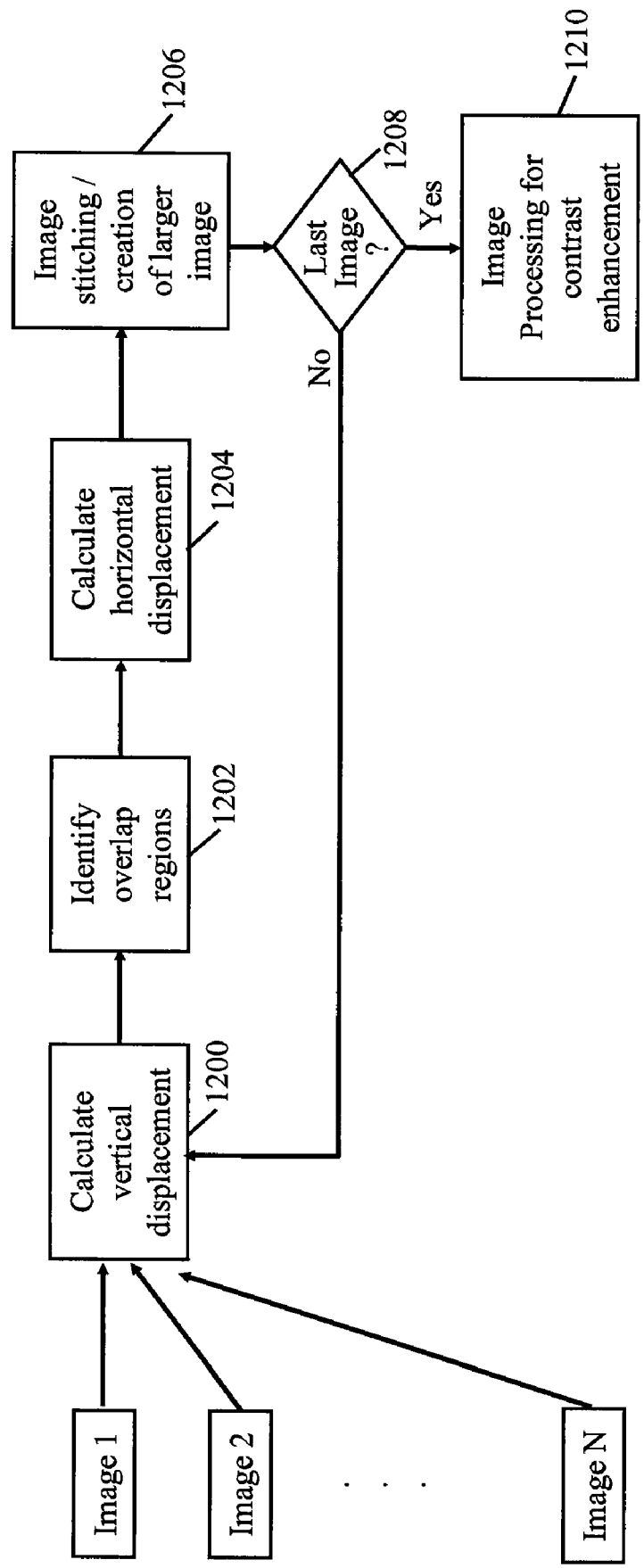
FIG. 13 is a logic flow diagram showing steps for image stitching according to one embodiment.

Processing steps of the stitching method are generally shown in the logic flow diagram of FIG. 13. The stop positions of the detector are known parameters, and are used as the vertical displacement between two adjacent sub-images 1100 in a calculate vertical displacement step 1200. The overlap between the sub-images is calculated for each sub-image based on vertical displacement and the actual physical size of the detector (X) in a transport direction in an identify overlap regions step 1202:

$$R_n = X/2 - (H_{n+1} - H_n)/2, \text{ where } n = 2, 2, \ldots N.$$

A calculate horizontal displacement step 1204 is executed. The regions between two adjacent sub-images are merged such that the two sub-images are stitched together to create a larger composite image. Image pixels in the overlap regions 1120 (FIG. 12) may not all be suitable for stitching. For example, some can be near or outside the collimation field, and some can have duplicate values. To automatically remove the unsuitable/undesirable pixels and create a seamless composite stitched image, in one preferred embodiment of the invention, the maximum intensity projection method is used to select an appropriate image pixel value for the stitched image. If the two overlap regions are substantially exactly aligned in both x and y directions (that is, that the anatomical features recorded in the two overlap regions are the same, pixel by pixel, among the two pixels), the one with the greater value (e.g., corresponding to higher exposure level) is used in the final stitched image in an image stitching step 1206 (FIG. 13).

In practice, the detector pixel matrix may not be exactly aligned along the detector transport axis. In this situation, the two adjacent sub-images can appear to have a slight horizontal (e.g., perpendicular to detector transport axis) displacement. This displacement can be corrected prior to the images being stitched so that the anatomy does not have a discontinuity across the stitching seam lines 1130 (FIG. 12). In a preferred embodiment, the horizontal offset is calculated in calculate horizontal displacement step 1204 (FIG. 13) by finding a maximum of the correlation function of the two overlap regions, such as described in commonly assigned U.S. Pat. No. 6,895,106 entitled "METHOD FOR STITCHING PARTIAL RADIATION IMAGES TO RECONSTRUCT A FULL IMAGE" to Wang et al. incorporated herein by reference.

If more than two sub-images, the composite image stitched from the first and second sub-images can be stitched with a third sub-image using the same process. The process is repeated for each additional sub-image until the last sub-image is stitched and the final full composite image is created in a last image check step 1208 (FIG. 13).

It is noted that when a set of x-ray exposures is performed, the stitching can start as soon as the first two sub-images are captured. For example, stitching can occur in parallel to the x-ray exposure such that the final stitched image becomes available immediately after the last sub-image is captured.

The stitched full image can be processed with contrast enhancement in an image processing for contrast enhancement step 1210 (FIG. 13) for display on a PACS workstation or film print. Contrast enhancement can also be performed to the individual sub-images prior to stitching. In such a case, the individual sub-images can be rendered optimally but there may be some visible seam lines in the stitched image.

Referring again to FIG. 6, it is noted that optional image quality assurance (QA) step 512 and image output step 514 can be executed as part of long length image processing.

It is desirable to minimize exposure to internal organs that are most sensitive to x-ray radiation. For example for full-body imaging, it may be beneficial to minimize exposure levels provided to the heart, reproductive system, or other organs. In one embodiment, automatic exposure control (AEC) functions of the imaging apparatus are used for this purpose.

The method and apparatus of the present invention provides for fully automated operation using a digital radiography system. It provides advantages similar to full-length film imaging, as described with reference to FIG. 2. That is, the operator/technologist employing the system of the present invention can readily provide a single command to obtain a full-size digital x-ray exposure. The system automatically positions the x-ray source and detector suitably for obtaining each image in the exposure series, without requiring additional command entry from the operator.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, with reference to FIG. 14, transport apparatus 72 for moving x-ray emitter 70 into position may be any of a number of types of devices for providing translational or angular movement to the x-ray tube. Control logic processing components used for executing the procedures of the present invention could be embodied in a number of different ways, including distributed control by multiple processors.

Thus, what is provided is an apparatus and method for long length imaging using a digital radiography imaging apparatus.

PARTS LIST

10 Imaging apparatus
12 Radiation source
14 Subject
16 Scintillator screen
18 Control logic processor
20 Image sensing array
30 Detector
50 Imaging apparatus
52 Control panel
54 Control logic processor
56 Display
58 Start button
60 Cancel button
62 Collimator
64 Sensor
66 Actuator
70 X-ray emitter
72 Transport apparatus
80 Detector
82 Transport apparatus
100 Patient
101 X-ray tube
102 Exposure area
103 Film Cassette
200 Patient
201 X-ray tube first position
202 Exposure area
203 Detector first position
206 X-ray tube position
207 Exposure area
208 Detector second position
210 Axis of motion
211 Detector axis of motion
300 Patient
301 X-ray tube
302 X-ray
303 Detector
304 X-ray tube second orientation
305 X-ray second coverage
307, 308 Position
310 Point
311 Detector translation axis
400 Patient
401 X-ray tube
402, 405 X-ray exposure
403 Detector
404 Shutter
407, 408 Position
410 Focal point
411 Axis
500 Set up step
502 X-ray exposure technique set up step
504 Exposure initiation/interruption step
506 Motion control step
508 X-ray generator, AEC, detector, and image readout control step
509 Loop
510 Image storage, stitching, and processing step
512 Image QA step
514 Image output step
600 Exposure length
610 Effective exposure length
620 Exposure overlap
630 Number of exposures
640 Floor to top of radiation field
650 Floor to bottom of radiation field
660 Stop position
670 Effective exposure field size
700 Number of exposures
710 Top
720 Bottom
730 Overall exposure length
740 Exposure overlap required for stitching
750 Effective exposure field
760 Effective radiation field
770 Stop position
800 Effective radiation field
805 Collimator aperture size
810 Collimator aperture
820 X-ray tube
830 SIC
840 Focal spot
850 Collimator shutters
860 SID
870 Detector imaging plane
900 X-ray tube
910 Focal spot
920 Detector stop position
925 Exposure field top and bottom
930 Height
940 Angle
950 Offset
960 Collimator aperture
970 Central x-ray beam
1000 Collimator shutter travel axis
1000 Collimator shutter travel axis
1010 Detector travel axis
1020 Collimator shutter aperture
1030 X-ray tube
1040 Collimator shutter
1050 Focal spot
1060 Detector stop position
1070 Exposure field top and bottom
1080 Height of the tube focal spot relative to the floor
1090 Stop position of the shutter
1100 Individual images
1110 Stitched image
1120 Overlap region
1130 Stitching seam line
1200 Calculate vertical displacement step
1202 Identify overlap regions step
1204 Calculate horizontal displacement step
1206 Image stitching step 1208 Last image check step
1210 Image processing for contrast enhancement step

The invention claimed is:

1. A method for long length imaging with a digital radiography apparatus, comprising:
   accessing setup instructions for an image;
   determining a set of imaging positions for an exposure series according to the setup instructions;
   sensing an operator command; and
   responsive to the operator command, automatically capturing an image at each position of the set of imaging positions of the exposure series by automatically repeating the steps of:
   (i) positioning an x-ray source and a detector at a location corresponding to a specified position of the set of imaging positions;
   (ii) capturing an image from the detector at the location; and
   (iii) storing the image as a partial image; and
   generating a long length image by combining two or more partial images.

2. The method of claim 1 wherein sensing an operator command comprises accepting a keyboard command.

3. The method of claim 1 wherein sensing an operator command comprises accepting an audible command.

4. The method of claim 1 wherein sensing an operator command comprises accepting a touchscreen command.

5. The method of claim 1 wherein sensing an operator command comprises accepting a command entered using a switch.

6. The method of claim 1 wherein accessing setup instructions comprises obtaining data on collimator settings.

7. The method of claim 1 wherein positioning an x-ray source comprises translating an x-ray tube between two positions.

8. The method of claim 1 wherein positioning an x-ray source comprises adjusting an angular orientation of an x-ray source.

9. The method of claim 1 further comprising displaying the long length image on a display.

10. The method of claim 1 wherein determining the set of imaging positions comprises determining at least one exposure overlap dimension.

11. The method of claim 1 wherein capturing an image comprises using automatic exposure control to minimize exposure levels to a patient.

12. The method of claim 1 wherein positioning an x-ray source comprises adjusting a collimator aperture size.

13. The method of claim 1 wherein positioning an x-ray source comprises adjusting a collimator shutter position.

14. The method of claim 1 further comprising obtaining operator confirmation prior to capturing an image from the detector.

15. The method of claim 1 wherein sensing an operator command comprises obtaining a single command for obtaining a complete set of multiple images for a patient.

16. A method for long length imaging with a digital radiography apparatus comprising:
   accessing setup instructions for an the image;
   determining a set of imaging positions for an exposure series according to the setup instructions;
   sensing an operator command;
   responsive to the operator command, automatically capturing an image at each position of the set of imaging positions of the exposure series by automatically repeating the steps of:
   (i) positioning an x-ray source and a detector at a location corresponding to a specified position of the set of imaging positions;
   (ii) obtaining operator confirmation;
   (iii) subsequent to obtaining operator confirmation, capturing an image from the detector at the location; and
   (iv) storing the image as a partial image; and
   generating a long length image by combining two or more partial images.

17. An apparatus for long length imaging comprising:
   an x-ray source having a collimator for providing an adjustable image field;
   a field translation apparatus for changing the position of the image field;
   an x-ray detector;
   a control logic processor in communication with the field translation apparatus for providing movement commands to the field translation apparatus to capture a series of partial images from the x-ray detector;
   means for generating a long length image by combining the series of partial images; and
   a control panel comprising (a) a start control for initiating automated imaging operation and (b) a cancel control for terminating imaging operation.

18. The apparatus of claim 17 further comprising a display to display the long length image.

19. The apparatus of claim 17 further comprising at least one feedback sensor coupled to a collimator for the x-ray source.

20. The apparatus of claim 19 further comprising an actuator for changing the collimator position.

* * * * *